United States Patent [19]
Calatayud et al.

[11] Patent Number: 5,482,934
[45] Date of Patent: Jan. 9, 1996

[54] PREGNA-1,4-DIENE3,20-DIONE-16-17-ACETAL-21 ESTERS, PROCESS FOR THEIR PREPARATION, COMPOSITION, AND METHODS FOR THE TREATMENT OF INFLAMMATORY CONDITIONS

[75] Inventors: Jose Calatayud; Jose R. Conde; Manuel Luna, all of Madrid, Spain

[73] Assignee: Especialidades Latinas Medicamentos Universales, S.A. (Elmu, S.A.), Madrid, Spain

[21] Appl. No.: 278,112

[22] Filed: Jul. 20, 1994

Related U.S. Application Data

[63] Continuation of Ser. No. 578,942, Sep. 7, 1990, abandoned.
[51] Int. Cl.⁶ .............................. A61K 31/58; C07J 71/00
[52] U.S. Cl. .............................. 514/174; 540/63; 540/70; 552/565; 552/566
[58] Field of Search ...................... 540/63, 70; 514/174; 552/565, 566

[56] References Cited

U.S. PATENT DOCUMENTS

| | | | |
|---|---|---|---|
| 3,079,384 | 2/1963 | Diassi et al. | 514/174 |
| 3,928,326 | 12/1975 | Brattsand et al. | 514/174 |
| 3,983,233 | 9/1976 | Brattsand et al. | 514/174 |
| 3,992,534 | 11/1976 | Brattsand et al. | 514/174 |
| 4,036,831 | 7/1977 | Loken et al. | 260/239.55 |
| 4,272,446 | 6/1981 | Riva et al. | 260/397.45 |
| 4,404,200 | 9/1983 | Thalen et al. | 540/70 |
| 4,695,625 | 9/1987 | MacDonald | 540/63 |
| 4,835,145 | 5/1989 | MacDonald | 514/174 |
| 4,925,933 | 5/1990 | Jakupovic et al. | 540/70 |

FOREIGN PATENT DOCUMENTS

| | | | |
|---|---|---|---|
| 2323215 | 5/1972 | Germany . | |
| 3012888 | 10/1981 | Germany | C07J 71/00 |
| 916996 | 7/1959 | United Kingdom . | |
| 1469575 | 4/1977 | United Kingdom | C07J 71/00 |
| 1504294 | 3/1978 | United Kingdom | C07J 5/00 |

OTHER PUBLICATIONS

Acta Pharmaceutica Suecicia, vol. 21, No. 2, 1984, pp. 109–124, (1984).
Acta Pharmaceutica Suecicia, vol. 19, No. 5, 1982, pp. 327–354 (1982).
Who Drug Information, vol. 3, No. 4, p. 210, (1989).
"Mechanisms of Glucocorticosteroid Action in Bronchial Asthma"; M. Kaliner J. Allerg. Clin Immunol 76:321–329 Aug. 1985.
"Basic Mechanisms of Asthma"; C. E. Reed Nov. 1988.
"Development of New Glucocorticosteroids with a very high ratio between Topical and Systemic Activities"; R. Brattsand et al. E. J. Resp. Disease. 1982.
"Bronchial Asthma and Glucocorticoids"; J. H. Toogood 1989.
"Tomorrow's Asthma Therapy–Are antiasthmatics in the 90ties Anti–inflammatory drugs?"; I. Szelenyi 1991.
"Correlation Between Chemical Structure, Receptor Binding, & Biological Activity of Some Novel, Highly Active, . . . "; E. Dahlberg et al. 1984.
"Flunisolide: A Review of its Pharmacological Properties & Therapeutic Efficacy in Rhinitis", G. E. Pakes et al. 1980.
"Budesonide: A Preliminary Review of its Pharmacodynamic Properties & Therapeutic Efficacy in Asthma and Rhinitis"; S. P. Clissold et al. 1984.
"Some Effects of Hydrocortisone on the Early Development of the Rat Cotton Pellet Granuloma"; P. C. Freeman et al. 1979.
"Corticosteroid Aerosols in the Treatment of Asthma"; C. S. Ted Tse et al. Pharmacotherapy 1984.
"General Pharmacology of Glucocorticoids"; S. J. Szefler. 1989.
"Farmacologia De Las Suprarrenales"; *Goodman & Filman*, 6th Edition, 1980.
"Glucocorticoid Physiology & Homeostatis in Relation to Anti–inflammatory actions"; A. Munck et al. 1989.
"Molecular Biology of Glucocorticoid Hormone Action"; M. C. LaPointe et al. 1989.
"Pharmacokinetic Studies of a Potent Glucocorticoid (Budesonide) in Dogs by by High–Performance Liquid Chromatography"; A. Ryrfeldt et al. 1979.
"Synthesis & Evaluation of Anti–inflammatory Activities of a Series of Corticosteroid 17 α–Esters Containing a Functional Group"; H. Ueno et al.
"Corticoides sistémicos y asma"; G. M. Cochrane 1979.

Primary Examiner—Mukund J. Shah
Assistant Examiner—Matthew V. Grumbling
Attorney, Agent, or Firm—Jacobson, Price, Holman & Stern

[57] ABSTRACT

The present invention relates to compounds of the formula:

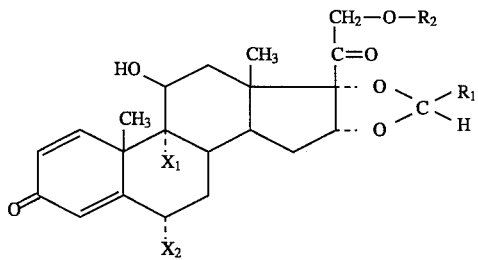

in which $X_1$ and $X_2$ correspond to H or F without distinction; $R_1$ represents the following radicals:

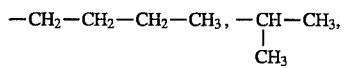

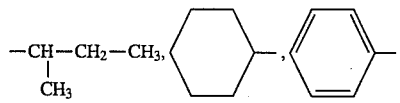

and $R_2$ represents the radicals

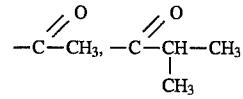

in the form of an R epimer, an S epimer, or a stereoisomeric mixture of the R and S epimers in terms of the orientation of the substituents on the carbon atom at position 22, novel intermediates and a method of their preparation by hydrolysis-ketalization, and use of such compounds as drugs and/or therapeutic agents.

12 Claims, No Drawings

PREGNA-1,4-DIENE3,20-DIONE-16-17-ACETAL-21 ESTERS, PROCESS FOR THEIR PREPARATION, COMPOSITION, AND METHODS FOR THE TREATMENT OF INFLAMMATORY CONDITIONS

This application is a continuation of application Ser. No. 07/578,942, filed Sep. 7, 1990 now abandoned.

The present invention has as its object to present pharmacologically active compounds and a process for the obtainment of said compounds and their intermediates. The invention also describes pharmaceutical compositions containing the said compounds and their use in the treatment of inflammatory conditions.

The purpose of the invention is to provide in addition certain glucocorticoids which have a combination of high anti-inflammatory activity at the application site and a low systemic glucocorticoid activity.

Since Kendall and Reichstein discovered the efficacy of cortisone in the treatment of rheumatoid arthritis (which earned them the Nobel prize), efforts have been multiplied to determine the basic structure responsible for the glucocorticoid effect and, likewise, its metabolism and mechanism of action. Since that time there have been numerous different synthetic materials which improve on the activity potential of the first product identified.

The clinical efficacy of the corticosteroids has resulted in their isolation, identification, and synthesis. The manipulation of their basic structures has permitted a wide variety of synthetic analogs, in which there has been an ongoing search for greater efficacy and an increase in the therapeutic effect/adverse systemic reaction ratio.

The toxicity effects have not been diminished, and it is important in this regard to point out that the corticosteroids are products with a clear pharmacologic effect, but with a strong power of accumulation in various tissues, which may pass unnoticed until the abrupt occurrence of a catastrophe.

In all the products studied, the therapeutic effects and the effects on the protein and carbohydrate metabolism have appeared concurrently, giving the impression that the effects sought and the adverse reactions are mediated by the same type of receptors, and that these receptors are identical for all corticosteroids.

Changes in molecular structure may cause variations in biologic activity of the corticosteroids, as a consequence of changes in absorption, protein binding, metabolism, excretion, bioavailability, and intrinsic activity in the biophase.

The introduction in -the 50's of systemic corticosteroids for the treatment of asthma constituted a milestone that was overshadowed by the appearance of side effects. This fact led to the use of corticosteroids by inhalation, since it was thought that by reducing the quantity of drug necessary to control the symptoms, it would in turn be possible to reduce the side effects. The first corticosteroid preparations developed in aerosol form were accompanied by varying efficacy and systemic side effects.

The appearance of high-activity derivatives permitted the preparation of topical formulations, with a high relative activity, combined with a low systemic action. There are two reasons for this behavior: 1) although the products can be absorbed topically, they are rapidly metabolized to less active forms; 2) the doses recommended are those which do not produce a systemic effect, not suppressing the hypothalamo-pituitary-adrenal axis within the therapeutic range used.

The corticosteroids used in aerosol form that have shown a highly positive effect are: beclomethasone dipropionate, betamethasone valerate, budesonide, flunisolide, and triamcinolone acetonide.

This philosophy of attempting to separate the local from the systemic effects has prompted the investigation of a series of corticosteroid derivatives with a distinct topical action and little or no systemic effect.

The goals of this series are decisively affected by the following factors:
a) High concentration in biophase (pulmonary or cutaneous superficial receptors)
b) Little topical absorption
c) Little gastrointestinal absorption
d) High sensitivity to hepatic oxidases and other inhibitory enzymes
e) Short half-life
f) Low intrinsic or systemic activity It has been the purpose of this invention to approximate as closely as possible that drug in which all of the preceding factors merge together to produce the ideal topical corticosteroid, in the knowledge that despite its drawbacks, this therapeutic agent continues to have a great future ahead of it.

A plan has been devised to find certain corticosteroid derivatives which combine intense topical pharmacologic activity with no or minimal systemic effects.

In the synthesis of 16,17-acetals of corticosteroids a mixture of epimers is obtained in relation with the formation of a new asymmetric center at C-22. The separation of the two epimers takes place through column chromatography (LC) or preparative HPLC techniques, which makes it difficult to apply industrially due to the limited quantities of product that can be treated in each unit process. In the process presented here, one of the epimers (22S)- (the most active epimer) is obtained through the hydrolysis-ketalization process from esters formed on the C-16, C- 17, and C-21 hydroxyls, wherein the ester at C-21 does not undergo hydrolysis. According to the catalyst selected it is possible to choose between obtainment of the mixture of epimers (22R,S)- or the selective obtainment of the (22S)- epimer. No process of this type has been described. European Patent Application No. 0 164 636 offers a process of transketalization from acetonides by conversion of these acetonides into acetals in the presence of aldehydes and hydrofluoric or hydrochloric acid in aqueous medium. Basically, hydrofluoric acid is used at temperatures generally ranging between 0° and −30° C., obtaining epimers of the acetals formed. No further references which describe selectivity toward one epimer or the other have been found.

The process that is the object of the invention offers [the possibility of] obtaining the (22S)- epimer or (22R,S)- mixtures of acetals from triesters previously selected while maintaining the desired radical at C-21, with these esters being easy to obtain. .The process is performed at room temperature, using solutions of dry HCl in anhydrous organic solvents. Obtainment of the R epimer is handled by preparative HPLC chromatography starting with the (22R, S)- mixture.

The steric hindrance of the acyl radical introduced and specific catalyst, makes difficult the formation of the (22S)- epimer. If the catalyst selected is extremely active, mixtures of those isomers are obtained. This hinderance characteristic is accompanied by an increase in reaction time, but does not cause a deterioration in formation of the final product by hydrolysis, secondary reactions, etc., under the conditions according to which the process takes place.

The process does not use highly corrosive or dangerous reagents, as is the case with hydrogen fluoride, nor extreme temperatures (below zero), features that are more useful for production at the industrial level.

The compounds according to the invention are characterized by the formula:

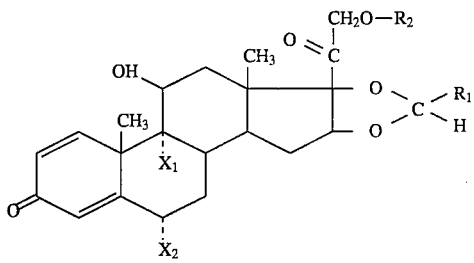

in which $X_1$ and $X_2$ correspond to H or F without distinction; $R_1$ represents the following radicals:

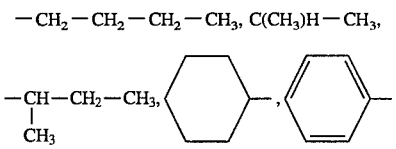

[and] $R_2$ represents the radicals

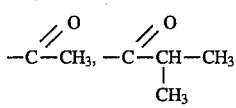

Each of these compounds has 2 stereoisomer components (epimers), which in relation to the general formula (I), may be represented in the following manner:

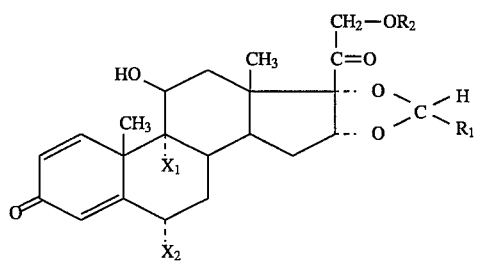

(S epimer)

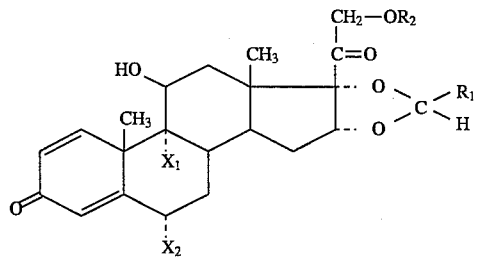

(R epimer)

In the diasteroisomers (II) and (III), the different configuration corresponds to C-22 (asymmetric carbon). These diasteroisomers take the name S and R epimers.

The compounds of this invention are prepared by hydrolysis-ketalization—with a suitable adequate catalyst which will be indicated in the corresponding cases—from the compounds triesterified at C-16, C-17, and C-21, whose structure is indicated below:

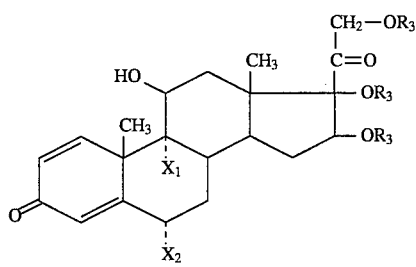

in which $R_3$ corresponds to an acetyl or oxo-isobutyl or isobutyryl radical and $X_1$ and $X_2$ represent H or F without distinction.

The intermediate compounds of formula IV are prepared from their corresponding hydroxylated derivatives by acylation of the appropriate anhydride in basic medium. These derivatives correspond to those with esterified hydroxyls on the carbons C-16, C-17, and C-21. The hydroxyl on carbon 11 is not esterified under the conditions whereby acylation takes place; only with certain anhydrides are small quantities on the order of 1% produced, which are treated as impurities and as such are eliminated during purification. If the quantity of anhydride present in the reaction is controlled, the ester formed on the hydroxyl of C-11 is produced in trace amounts. Thus, the number of moles of the corresponding anhydride should not exceed 25 times the number of moles of corticosteroid, so that acylation does not take place on the C-11 hydroxyl or is as restricted as possible, as has been indicated previously. The temperature of the reaction is another important factor, and the ideal conditions for acylation of the C-21, C-16, and C-17 hydroxyls are temperatures in the 15°–45° C. range. Above this temperature, a larger proportion of tetraacylated product may be obtained.

The reaction time should not exceed four hours, and the proper time for the majority of the corticosteroids and anhydrides used is from 1.5 to 2 hours.

Pyridine, dioxane, or DMSO are preferable as solvents over other possible products to obtain a greater solubility and, in particular, pyridine is the most appropriate because of its intrinsic basic character.

Once acidified and extracted with organic solvents immiscible with water, the reaction mixture is concentrated, washed, and recrystallized to obtain the corresponding compound, acylated on the C-16, C-17, and C-21 hydroxyls.

Purification by the washing and recrystallization method used gives a purity greater than 95%, which is useful for application as an intermediate product in the process for formation of the acetal according to the procedure that is the object of the invention.

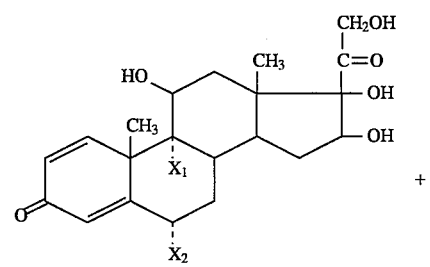

+

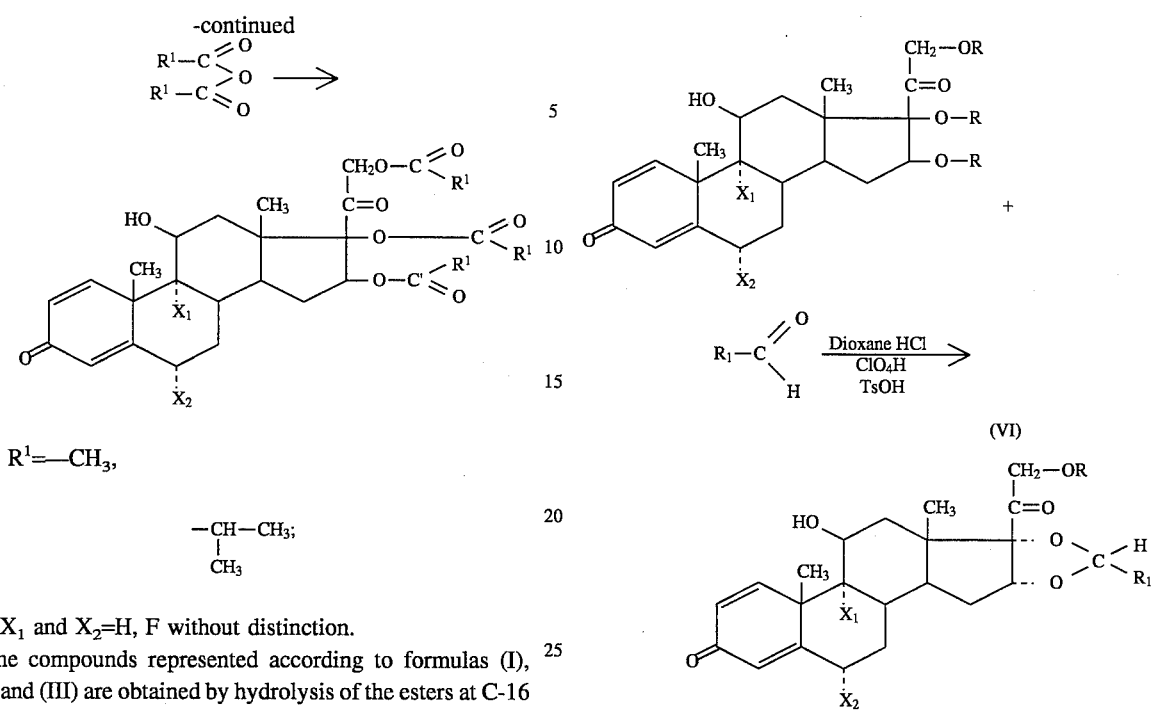

with $R^1$=—$CH_3$, $$-CH-CH_3;$$
$$\phantom{-}|$$
$$CH_3$$

and $X_1$ and $X_2$=H, F without distinction.

The compounds represented according to formulas (I), (II), and (III) are obtained by hydrolysis of the esters at C-16 and C-17 with hydrochloric acid dissolved in the solvent which is used as a vehicle for the reaction in anhydrous medium and with a specific catalyst to direct the ketalization reaction toward the S epimer (II) or mixture of the R and S epimers (II+III) in the presence of the corresponding aldehyde. Unless otherwise clear from the text, reference to HCl gas shall mean 13% (w/w) HCl gas.

The solvents generally used are: dioxane, methylene chloride, and chloroform, all anhydrous. However, dioxane is the most widely used for this type of reaction. The selection of the solvent has a bearing on the proportion of epimers in the mixture, as milder catalysts direct the reaction toward the production of a single epimer, while more active catalysts provide a mixture of isomers that approximates the ratio of 1/1. The selection of the solvent may slightly alter this proportion. According to the epimer ratio characteristics that it is desired to obtain, the catalysts used are p-toluensulfonic acid, yielding the S epimer as the major product in a yield of 98–99%, and perchloric acid in 70% solution in glacial acetic acid, yielding a mixture of both R and S epimers in a ratio of 40/60 without distinction.

On conducting the reaction without catalysis, the reaction times are greatly lengthened, and therefore it is not practical to carry out the reaction under these conditions; in addition, a larger quantity of impurities is obtained. In this case, one of the isomers, the S epimer, would be obtained, present as the major portion in comparison to the R epimer.

The reaction is carried out on C-16 and C-17 esters by hydrolysis in the presence of hydrochloric acid, with subsequent reaction of the aldehyde in these positions, to form the corresponding acetal. Therefore, selective hydrolysis takes place, since the ester formed at C-21 is not hydrolyzed under the conditions mentioned, so that the triester should be chosen in order to keep the radical which is of interest at C-21.

in which R corresponds to an acetyl or oxo-isobutyl or isobutyryl radical. $R_1$ represents the following radicals:

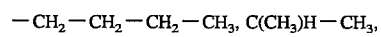

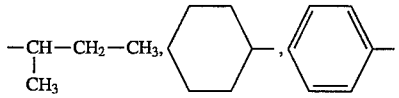

The reaction is conducted at room temperature (10°–20° C.), provided that the solubility of the triester used permits it. Temperatures above 25° C. activate secondary reactions and the partial deacylation of C-21.

The reaction time fluctuates between 100 and 200 hours, depending on the starting corticosteroids, the acylating agents, and the aldehydes used, and it is necessary to reach an equilibrium between the maximum formation of the epimer or mixture of epimers and the secondary reactions that occur.

Once the excess acid has been neutralized, the crude product is extracted with methylene chloride, and the organic phase is separated, then concentrated under vacuum. The product is crystallized from ethyl ether/petroleum ether and is finally purified by treatment in a chromatographic column with LH-20 or LH-60 Sephadex as a stationary phase and a mixture of organic solvents, e.g. heptane/ethanol, or a mixture of organic solvents and water, in proportion which may range between 90/10 and 98/2 for heptane/ethanol and 70/30 for ethanol/water, as a mobile phase. There may also be subsequent purification procedures involving washing or reprecipitation with solvents such as methanol, ethanol, acetone, dioxane, ethyl acetate, water etc. By using these one at a time or in binary or ternary mixtures such as dioxane/water or ethanol/acetone/water in appropriate proportions, purification son the order of 99.5–99.9% are obtained. Thus in our case, we achieved a purification process with ternary mixtures of ethyl alcohol/acetone/water which, by dissolution of the product in organic solvents and subsequent precipitation by addition of the corresponding proportion of water under very specific, very vigorous agitation conditions and very slow addition time, among other factors, results in purification from an 85-90% starting point to 99.99% purity.

Purification by column chromatography is not suitable for industrial production. In this type of operation there are usable fine industrial purification methods which make the obtainment process for this type of compound very complete.

Depending on the application site, and with the purpose of achieving optimal availability of the active ingredient, different galenical formulations have been prepared for topical administration of the compounds according to this invention.

Optimal availability for percutaneous formulations is achieved with a system of glycol-based solvents (propylene glycol and 1,3-butanediol) alone or in combination with water. It is also possible to dissolve the steroids completely or partially in a lipophilic phase, with the aid of a surfactant as a solubilizer. Percutaneous compositions come in the form of ointments, oil-water cream, water-oil cream or lotion. The active principle may be present in the previous pharmaceutical compositions in solution, in continuous dispersed phase, or as micronized solids.

The aerosol system is designed in such a way that each delivered dose contains 10–1000 µg (preferably 20–250 µg) of the active steroid. The most active steroids are administered in the lower part of the dosage range. The micronized steroid must be in particles substantially smaller than 5 µm. In the pressurized aerosol, the substance is suspended in a propellant gas mixture with the assistance of a dispersant, such as sorbitan trioleate, oleic acid, lecithin, or sodium salt of dioctylsulfosuccinic acid.

The invention will be further illustrated by the following non-limitative examples. The molecular weights of the corresponding products have been confirmed by mass spectrometry, and the melting points (uncorrected) determined with a Buchi unit. The HPLC analyses were performed under the following conditions:

| | |
|---|---|
| Apparatus: | Hewlett-Packard 1084 A |
| Detector: | UVD (243 mn vx. 430 nm) |
| Column: | 200 × 4.6 mm |
| Stationary phase: | Lichrosorb C18 (5 µm) |
| Mobile phase: | Ethanol: Water (0.5 ml/min) |
| Temperature: | 35° C. |
| Injection: | 5 µl ethanol sol. at 2 mg/ml |

SYNTHESIS OF TRIACYLATED DERIVATIVES C-16, C-17, AND C-21

EXAMPLE I

Preparation of pregna 1,4-diene-3,20-dione, 16,17,21-tris-(2-methyl-1-oxo-propoxy)- 11-hydroxy (11β,16α)

30 ml pyridine and 21.6 g isobutyric anhydride (equivalent to 0.13 moles) are placed in a 500 ml reactor equipped with mechanical agitation; while agitating vigorously, 10 g (0.026 mole) pregna-1,4-diene-3,20-dione, 11,16,17,21-tetrahydroxy (11β,16α) are added gradually in portions at room temperature. The corticosteroid addition time corresponds to approximately 25–30 min. Once the said corticosteroid has been dissolved at room temperature, agitation is continued for a period of time ranging between 1.5 and 2 hr until esterification of the hydroxyls at C-21, C-16 and C-17 is complete. Upon completion of the reaction, 150 ml of a 10% aqueous solution of HCl are added, and agitation of the reaction mixture is continued for 30 min.; subsequently, the said mixture is treated three times with the 88 ml methylene chloride in order to extract the triester, and the organic phase is washed three times with 100 ml water each time. The solution is concentrated under vacuum in a rotary evaporator, and produces a crude product which is treated with 50 ml ethyl ether and 200 ml petroleum ether (fraction 40/60). Agitation of the precipitate obtained is continued for 1 hr., and finally the product is filtered and recrystallized with petroleum ether (40/60/ethyl ether 4/1, obtaining a yield of 13.3 g and a purity of 97.5– 98%.

TLC: Toluene/ethyl acetate 30/40, Rf=0.61.

EXAMPLE II

Preparation of pregna 1,4-diene-3,20 dione-16,17,21-tris-(2-methyl-1, oxo-propoxy)- 6,9-difluoro-11-hydroxy (6α,11β,16α)

80 ml pyridine 19.2 g (0.12 mole) isobutyric anhydride are placed in a 500 ml reactor, and gradually, with the reaction mixture maintained at 40° C., 10 g (0.024 mole) pregna-1,4-diene-3,20-dione, 6,9-difluoro-11,16,17,21-tetrahydroxy (6α,11β,16α) are introduced in such a way that no further quantity is added until the previous portion has dissolved. The fluocinolone dissolution time is equivalent to approximately 2 hr. Once dissolved, agitation of the solution is continued for 3 hr. at 40° C. The TLC of the reaction mixture indicates when all of the corticosteroid has reacted. Once the indicated time has elapsed, the product is cooled and 80 ml of an aqueous solution of 10% hydrochloric acid ar added after cooling has been achieved. The reaction mixture is extracted 4 times with 40 ml chloroform each time, the chloroform extract is washed 4 times with 40 ml water, and the extract is dried over $MgSO_4$. It is then brought to dryness in a rotary evaporator, and precipitated and recrystallized with ethil ether petroleum ether (40/60 fraction), obtaining a yield of 12.1 g and a purity of 95%.

TLC solvent: toluene/ethyl acetate 30/40, Rf=0.48.

EXAMPLE III

Preparation of pregna 1,4-diene-3,20-dione, 16,17,21-tris-(2-methyl-1-oxo-propoxy)- 9-fluoro-11-hydroxy-(11β, 16α)

The process applicable to the triester of triamcinolone isobutyrate is similar to the preceding process.

EXAMPLE IV

Synthesis of pregna 1,4-diene-3,20-dione, 16,17,21-tris-(acetyloxy)-11-hydroxy-(11β,16α)

In a 500 ml reactor equipped with a mechanical agitator and addition funnel, 10 g (0.026 mole) pregna- 1,4-diene-3,20-dione, 11,16,17,21-tetrahydroxy (11β,16α) are dissolved in 30 ml pyridine with vigorous agitation. 13.5 g (0.13 mole) acetic anhydride are introduced in such a way that the addition takes place within 10 min. and the temperature of the reaction mixture does not exceed 20° C. Once the acetic anhydride has been added, agitation is continued for 1 hr. (TLC or HPLC on a sample will indicate the end of the reaction by the disappearance of the starting corticosteroid). The reaction time should not be extended beyond the indicated period in order to prevent acylation on the C-11 hydroxyl. Upon completion of the reaction, 130 ml of a 10% aqueous solution of HCl are added, maintaining the reaction mixture for 30 min. with agitation. Subsequently, three times, 75 ml methylene chloride (each time) are added to extract the triester formed. The solution of the organic extract is washed 3 times with 100 ml water (each time), and is maintained for 12–14 hr. with anhydrous $MgSO_4$ to dry the said solution.

Concentration to dryness of the organic extract gives an oil which is treated with ethyl ether/petroleum ether (40/60 fraction) 1/3. The precipitate obtained is recrystallized from methylene chloride/petroleum ether 1/4, obtaining 12.5 g pregna-1,4-diene-3,20-dione, 16,17,21-tris-(acetyloxy)-11-hydroxy (11β,16α) of 98–98.5% purity.

EXAMPLE V

Formation of pregna 1,4-diene- 3,20-dione-16,17,21-tris (acetyloxy)-6,9-difluoro- 11-hydroxy-(6α,11β,16α)

10 g pregna-1,4-diene-3,20-dione-6,9-difluoro- 11,16,17, 21-tetrahydroxy-(6α,11β,16α) (0.024 mole) are dissolved in 110 ml pyridine heated to 50° C. to facilitate dissolution in a 500 ml reactor, equipped with mechanical agitation, a thermometer, and an addition funnel; the mixture is cooled, and once the corticosteroid is completely dissolved, 19.4 g (0.19 mole) acetic anhydride are slowly added with vigorous agitation (45° C.), continuing to stir for 3 hr. and subsequently for 1 hr. more at 45° C. This time period can be extended somewhat. A sample in TLC or by HPLC will indicate the end of the reaction. Subsequently, 300 ml aqueous solution of 10% HCl are introduced, continuing to stir the mixture for 45 min.; finally, the triester formed is extracted three times with 80 ml methylene chloride (each time), and the organic extract is kept over $MgSO_4$. The solution is evaporated to dryness, and the oil obtained is treated with 50 ml ethyl acetate and 150 ml petroleum ether (40/60 fraction) with agitation for 1 hr.

The precipitate obtained is recrystallized in ethyl ether/ petroleum ether 1/4, obtaining 11.8 g pregna-1,4-diene-3, 20-dione-16,17,21-tris-(acetyloxy)- 6,9-difluoro-11-hydroxy-(6α,11β,16α) with a purity of 96.5%.

EXAMPLE VI

Preparation of pregna 1,4-diene-3,20-dione, 16,17,21-tris-(acetyloxy)-9-fluoro- 11-hydroxy (11β,16α)

This synthesis takes place in the same way as indicated previously, giving similar yields and purities.

When the triacylated derivatives are treated with dioxane, containing 13–15 wt % HCl gas in solution and the corresponding aldehyde in the presence of 70% perchloric acid in glacial acetic acid as a catalyst, under the temperature and time conditions specified in the following examples, the corresponding acetal is obtained on the C-16 and C-17 hydroxyls, with a mixture of R and S epimers which fluctuates between 40/60%, 50/50% according to the conditions under which the reaction is conducted. If, in contrast, p-toluenesulfonic acid is used as a catalyst instead of the perchloric acid mentioned earlier, the S epimer is obtained predominantly in a quantity of 95–98%. In both cases, the ester at C-21 does not undergo hydrolysis.

The structure of the synthesized compounds and their most significant spectroscopic characteristics are summarized in Table I.

The processes for obtainment of mixture of epimers and processes for formation of the S epimer are described separately in the following non-limiting examples of the invention.

FORMATION OF (22R,S-) AND (22S)- DERIVATIVES

EXAMPLE VII

Synthesis of (22R,S)- pregna 1,4-diene-3,20-dione, 16,17-[ [cyclohexylmethylidyne]bis (oxy)] -11-hydroxy-21-(2-methyl-1-oxo-propoxy)-(11β,16α)

55 ml anhydrous dioxane are placed in a 500 ml reactor provided with mechanical agitation and an addition funnel, and 8 g (0.014 mole) pregna-1,4-diene 3,20-dione, 16,17, 21-tris-(2-methyl-1-oxo-propoxy)- 11-hydroxy-(11β,16α) and 4.3 g (0.038 mol) of cyclohexane carbaldehyde are dissolved in it; subsequently the mixture is stirred for 30 min., and 45 ml dioxane HCl containing 13% HCl gas are added slowly, and finally, dropwise, 1 ml 70% perchloric acid in glacial acetic acid (taking on a reddish color) is kept for 190 hr. with agitation and then heated to 40° C. for 12 hr. It is possible to estimate whether the reaction is complete with an aliquot of the reaction product, analyzing a sample by HPLC under the conditions stipulated below.

Once the triester has disappeared from the reaction mixture, the reaction is considered to be terminated; adding 200 ml methylene chloride, the mixture is treated with 500 ml 5% $K_2CO_3$ in aqueous solution, with vigorous agitation in a separatory funnel, and the organic mixture is washed three times with 80 ml water (each time). Once decanted, the organic phase is kept over on anhydrous $MgSO_4$ for drying, and is concentrated to dryness on a rotary evaporator; an oil remains, which upon treatment with 25 ml methylene chloride and 150 ml petroleum either (40/60 fraction) yields 8.52 g crude product which is purified either by recrystallization in ethyl ether/petroleum ether or by passing through a column with Sephadex LH-20 as the stationary phase and ethanol-free chloroform as the mobile phase, obtaining 8 g (22R,S)-pregna-1,4-diene-3,20-dione, 16,17-cyclohexyl-methylidyne-bis(oxy)-11-hydroxy-21-(2-methyl- 1-oxo-propoxy)-(11β,16α) in a purity of 98.5–99% and with an epimer proportion of 45/55% to 50/50%.

The mixture of epimers is resolved by preparative HPLC, using a 7 μm Lichrosorb RP-18 column (250×10 mm i.d.) and ethanol/water as the mobile phase, and obtaining the (22R)- epimer practically pure and the (22S)- epimer in a purity greater than 99%.

The product containing the (22R,S)- mixture can also be purified without having to use column chromatography by a method which is described in the following example.

EXAMPLE VIII

Obtainment of (22,S)- pregna 1,4-diene-3,20-dione 16,17-[ [cyclohexyl-methylidyne]bis (oxy)]- 11-hydroxy-21-(2-methyl-1-oxo-propoxy)-(11β,16α)

55 ml anhydrous dioxane are placed in a 500 ml reactor and 8 g (0.014 mole) pregna-1,4-diene-3,20-dione, 16,17, 21-tris-(2-methyl-1-oxo-propoxy)-(11β,16α)- and 4.3 g (0.038 mole) cyclohexane carbaldehyde are dissolved, next adding 1 g p-toluenesulfonic acid and 50 ml dioxane-HCl (containing 13% HCl gas), which is introduced slowly over a period of 30 min. Agitation is continued for 200 hr., and the end of the reaction may be estimated by analyzing the mixture of HPLC under the conditions indicated below. Once the acetal is formed, 200 ml $CL_2CH_2$ are added to the reaction mixture and treated with 500 ml 5% $K_2CO_3$ in aqueous solution to eliminate the acidity. Following this elimination, the product is washed three times with 80 ml water; the solution is dried over $MgSO_4$ and brought to dryness in a rotary evaporator. The oil obtained is treated with 25 ml $CL_2CH_2$ and 50 ml petroleum ether (40/60 fraction). The solid collected, 5.3 g, is purified by the method described below.

5.2 g of crude are dissolved in 300 ml 96° ethanol and 50 ml acetone in a 500 ml flask provided with vigorous mechanical agitation and an addition funnel. 80 ml water are slowly added dropwise with vigorous agitation, so that the addition process is completed within 6 hrs. Once all the water has been added, the precipitate formed is stirred for 2 hrs., filtered and washed with water, and the product dried in a 40° oven, obtaining 4.5 g (22S)- pregna-1,4-diene,3,20-dione, 16,17-cyclohexylmethylidyne-bis(oxy)-11-hydroxy-21-(2-methyl-1-oxo-propoxy)-(11β,16α) in a purity greater than 99%.

This method is extended, with small variations, to purification of the remaining compounds, and is not limited to the examples indicated. It is also possible to employ column purification using Sephadex LH-20 as the stationary phase and ethanol-free chloroform as the mobile phase. Within this purification there is a first very pure fraction of the S epimer and a second fraction in which the ratio of R and S isomers may fall in the range of 2/98%, respectively.

EXAMPLE IX

Formation of (22R,S)- of pregna 1,4-diene- 3,20-dione-21-(acetyloxy)-11-hydroxy-16,17-(pentylidene) bis(oxy)-(11β,16α)

8 g (0.016 mole) pregna-1,4-diene-3,20-dione- 16,17,21-tris-(acetyloxy)-11-hydroxy-(11β,16α) are dissolved in 60 ml anhydrous dioxane in a 500 ml flask, provided with a thermometer, mechanical agitation, an addition funnel and waterbath; subsequently, 4 g (0.046 mole) valeraldehyde are added and, slowly, dropwise, with vigorous agitation, 60 ml dioxane HCl (containing 13% HCl gas). Once addition of the dioxane is complete, 1 ml 70% perchloric acid in glacial acetic acid is introduced, heating the product to 50° C. for 200 hrs. Running a sample through TLC or HPLC will indicate whether the reaction is complete by the appearance of two peaks of the epimers and the disappearance of the triester of the reaction. Upon completion of ketalization, 175 ml chloroform are added, vigorously agitating the mixture in a separatory funnel with 510 ml aqueous solution of 5% $K_2CO_3$. If a pH below 6 persists in the organic phase, additional treatment with an aqueous solution of $K_2CO_3$ is performed until the excess acidity is eliminated. The organic phase is washed three times with 100 ml water (each time), and is kept for 14 hr. over $MgSO_4$; the filtered organic phase is brought to dryness in a rotary evaporator, yielding an oil which when treated with 50 ml ethyl ether and 170 ml petroleum ether (40/60 fraction) gives a crude solid of 6.5 g.

The following procedure is performed for the purification of this product:

A mixture of 39 ml acetone, 65 ml 96° ethanol, and 104 ml water are placed in a 250 ml flask, and 6.5 g of the crude product obtained previously are suspended while agitating vigorously, and this agitation is continued for 3 hr.; the product is then filtered, washed with water, and dried in an oven at 45° C., giving 5.7 g (22R,S)- pregna-1,4-diene-3, 20-dione, 21-(acetyloxy)- 11-hydroxy-16,17-(pentylidene)-bis-(oxy)-(11β,16α) in a purity of 99.5%. The ratio of R/S epimers is 45/55.

The resolution of the epimers is achieved similarly according to the characteristics indicated in Example VII.

EXAMPLE X

Formation of (22S)- pregna 1,4-diene-3,20-dione- 21-(acetyloxy)-11-hydroxy- 16,17-(pentylidene)-bis-(oxy)-(11β,16α)

8 g (0.016 mole) pregna-1,4-diene-3,20-dione, 16,17,21-tris-(acetyloxy)-11-hydroxy-(11β,16α) are dissolved in 65 ml anhydrous dioxane in a 500 ml reactor provided with mechanical agitation and an addition funnel, and subsequently 4 g (0.046 mole) valeraldehyde and 1.2 g p-toluenesulfonic acid are introduced, followed by the dropwise addition with vigorous agitation of 60 ml dioxane-HCl (13 wt % HCl). Once added, agitation of the product is continued at 50° C. for the period of time necessary for the triester to disappear from the reaction mixture. The reaction is followed by HPLC, whereby the formation of the S epimer is visualized perfectly. TLC only reveals elimination of the triester, so that the first method is more advisable. The reaction time fluctuates between 100 and 150 hr. The reaction mixture is then treated with 120 ml chloroform and 60 ml methylene chloride. The organic solution is treated with a 5% $K_2CO_3$ solution in order to eliminate the excess acidity and is washed three times with water; the residual water is eliminated by allowing it to stand over anhydrous $MgSO_4$. The organic phase is brought to dryness, and the crude product in the form of an oil is treated with a mixture of 25 ml ethyl ether, 25 ml methylene chloride, and 175 ml petroleum ether (40/60 fraction). 4.5 g solid are obtained, which is purified according to the method followed in the preceding example.

EXAMPLE XI

Formation of (22R,S)- pregna 1,4-diene- 3,20-dione-16,17-(cyclohyxyl methylidine)-bis-(oxy)-6,9-difluoro-11-hydroxy-21-(methyl- 1-oxo-propoxy)-(11β,16α)

100 ml anhydrous dioxane heated on a water bath to 35° C. are placed in a 500 ml reactor equipped with a water bath, addition funnel, and mechanical agitation; under agitation, 8.8 g (0.014 mole) pregna- 1,4-diene-3,20-dione, 16,17,21-tris-(2-methyl-1-oxo-propoxy)- 6,9-difluoro-11-hydroxy-(6α,11β,16α) are added in small portions while agitating (a portion of the triester should not be added until the previous fraction has dissolved completely). Once all of the triester has been added and dissolved completely, the product is kept between 15°–18° C. for several minutes while agitating, and 4.5 g (0.04 mole) cyclohexane carbaldehyde and 1.1 ml 70% perchloric acid in glacial acetic acid are added. Finally, 50 ml anhydrous dioxane containing 13–14% HCl gas by weight is slowly added and continuously stirred at room temperature during the time necessary for the triester to disappear from the reaction mixture. Once the reaction is complete, 250 ml chloroform are added; the mixture is treated three times in a separatory funnel with 250 ml of a 5% aqueous solution of $K_2CO_3$ each, and washed again three times with 100 ml water each time. The organic phase is kept over anhydrous $MgSO_4$ or another suitable drying agent; the organic solution is concentrated to about ⅕ of its volume and is treated with 300 ml ethyl acetate, continuing to stir the mixture for 2 hr. at 30° C. Subsequently, the solution is cooled and kept overnight at −10° C. Finally, it is concentrated to dryness, and the oil obtained is treated with 50 ml ethyl ether and 180 ml petroleum ether. The solution is kept cold during 24 hr., yielding a precipitate of 7.5 g (22R,S)- pregna-1,4-diene-3,20-dione, 16,17-(cyclohexylmethylidine)-bis-(oxy)-6,9-difluoro- 11-hydroxy-21 (methyl-1-oxo-propoxy)-(11β,16α). This product can be purified by the method indicated in Example VIII, and in this manner a yield of 7 g is obtained, with a purity of 99–99.5% and a proportion of R/S epimers of approximately 40/60%.

The resolution of the epimers is achieved similarly according to the characteristics indicated in Example VII.

EXAMPLE XII

Formation of (22S)- pregna-1,4-diene- 3,20-dione-16,17-(cyclohexylmethylidine)-bis-(oxy)- 6,9-difluoro-11-hydroxy-21-(s-methyl- 1-oxo-propoxy)-(11β,16α)

120 ml anhydrous chloroform, 4,5 g (0.04 mole) cyclohexane carbaldehyde and 1 g p-toluenesulfonic acid are placed in a 1 L reactor provided with a water bath, a reflux condenser, a Dean-Stark trap, a magnetic stirrer, thermometer and addition funnel. While vigorously agitating and in aliquots 8.8 g (0.014 mole) pregna-1,4-diene-3,20-dione, 16,17,21-tris-(2-methyl- 1-oxo-propoxy)-6,9-difluoro-11-hydroxy (6α,11β,16α) are added in small aliquots in such a way that no new aliquot is added until the previous one has been dissolved. Finally, 100 ml chloroform containing HCl gas dissolved in an approximate proportion of 10 wt % are added, and the product is kept under vigorous agitation for 5 hr. at room temperature. Subsequently, the product is maintained under very mild reflux (water is collected in the Dean-Stark trap during the process) along the time necessary for the reaction to be completed, i.e., until no more triester exists in the reaction mass. This can be checked by taking a small sample from the reactor, first neutralizing it, and then estimating the end of the reaction by HPLC. It is advisable to add an additional 10–15 ml chloroform-hydrochloric acid during the process.

200 ml methylene chloride are added to the reaction mixture; the mixture is treated three times with 200 ml 5% $K_2CO_3$ in aqueous solution, and subsequently washed three times with 80 ml water each time. The organic solution is left overnight, drying with anhydrous $MgSO_4$ or another conventional drying agent, brought to dryness, and the oil obtained is treated with 200 ml toluene for 2 hr., with agitation. The oil is collected by decantation and is diluted in 50 ml methylene chloride and 20 ml tert-methyl-butyl ether, and the solution obtained is precipitated with 75 ml petroleum ether (40/60 fraction), increasing the quantity of the said ether (if necessary) up to the point of complete precipitation. It is advisable that he petroleum ether be added slowly, with vigorous agitation. The solid collected, 7.2 g, is purified by the following procedure. 7.2 g of the product obtained previously are dissolved in a flask which contains 150 ml 96° ethanol and 200 ml acetone; under stirring vigorously, 200 ml water are added slowly, dropwise, so that complete addition of the water is achieved within 6 to 7 hr. The precipitate formed is stirred for 2 hr., after which the precipitate obtained is filtered and washed with water and dried in a 40°–45° C. oven, given 6.5 g pregna-1,4-diene-3,20-dione, 6,17-(cyclohexylmethylidine)-bis(oxy)-6,9-difluoro- 11-hydroxy-21(2-methyl-1-oxo-propoxy)-(11β,16α) in a purity above 99%. The ratio of the R/S isomers corresponds to 1/99%, respectively.

A similar process is that followed in the formation of the different acetals of pregna-1,4-diene- 3,20-dione, 11,16,17,21-tetrahydroxy-(11β,16α), pregna- 1,4-diene-3,20-dione, 9-fluoro-11,16,17,21-tetrahydroxy-( 11β,16α), and pregna-1,4-diene-3,20-dione, 6,9-difluoro- 11,16,17,21-tetrahydroxy-(6α,11β,16α) with valeraldehyde, cyclohexanecarbaldehyde, benzaldehyde, isobutyraldehyde, and isovaleraldehyde for the formation of the 21-esters (22R,S)- (22S)- of the corresponding compounds, and it is possible by preparative HPLC to achieve the separation of (22R)- and (22S)- from the mixture.

The structure of the compounds synthesized and their most significant spectroscopic properties are compiled in Table II.

EXAMPLES OF PHARMACEUTICAL PREPARATIONS

The following and non-limitative examples illustrate the formulations intended for different topical forms of administration. The amount of active steroid in the percutaneous formulations are ordinarily 0.001–0.2% (w/w) preferably 0.01–0.1% (w/w).

| Formulation 1, Ointment | |
| --- | --- |
| Steroid micronized | 0.025 g |
| Liquid paraffin | 15 g |
| White paraffin a.d. | 100.0 g |
| Formulation 2, Ointment | |
| Steroid | 0.025 g |
| Propylene glycol | 6.0 g |
| Arlacel 83 (sorbitan sesquioleate) | 6.0 g |
| Liquid paraffin | 15.0 g |
| White paraffin a.d. | 100.0 g |
| Formulation 3, O/W Cream | |
| Steroid | 0.025 g |
| Cetyl alcohol | 7.0 g |
| Glyceryl monostearate | 4.0 g |
| Soft paraffin | 15.0 g |
| Polyglycol 1500 | 3.0 g |
| Citric acid | 0.1 g |
| Sodium citrate | 0.2 g |
| Propylene glycol | 20.0 g |
| Water a.d. | 100.0 g |
| Formulation 4, O/W Cream | |
| Steroid micronized | 0.025 g |
| Soft paraffin | 20.0 g |
| Liquid paraffin | 5.0 g |
| Cetyl alcohol | 5.0 g |
| Tween 65 | 3.0 g |
| Span 60 | 1.0 g |
| Citric acid | 0.1 g |
| Sorbic acid | 0.2 g |
| Sodium citrate | 0.2 g |
| Water a.d. | 100.0 g |
| Formulation 5, W/O Cream | |
| Steroid | 0.025 g |
| Soft paraffin | 35.0 g |
| Liquid paraffin | 8.0 g |
| Arlacel 83 | 5.0 g |
| Sorbic acid | 0.2 g |
| Citric acid | 0.1 g |
| Sodium citrate | 0.2 g |
| Water a.d. | 100.0 g |
| Formulation 6, Lotion | |
| Steroid | 0.025 g |
| Isopropanol | 50.0 ml |
| Carbopol 940 | 0.5 g |
| NaOH | q.s. |
| Water a.d. | 100.0 g |
| Formulation 7, Injectable suspension | |
| Steroid Micronized | 0.05–10 mg |
| Sodium carboxymethylcellulose | 7 mg |
| Sodium chloride | 10 mg |
| Tween 80 | 0.5 mg |
| Benzyl alcohol | 8 mg |
| Water for injection | 1.0 ml |
| Formulation 8, Pressurized Aerosol for Oral and Nasal Inhalation | |
| Steroid micronized | 0.1% w/w |
| Sorbiton trioleate | 0.7% w/w |
| Thrichloro-fluoromethane | 24.8% w/w |
| Dichloro-tetrafluoroethane | 24.8% w/w |
| Dichlorodifluoromethane | 49.6% w/w |
| Formulation 9, Solution for Atomization | |
| Steroid | 7.0 mg |
| Propylene glycol | 5.0 g |
| Water a.d. | 10.0 g |

-continued

| Formulation 10, Powder for Inhalation A capsule filled with a mixture of | |
|---|---|
| Steroid micronized | 0.1 g |
| Lactose | 20 mg |

PHARMACOLOGIC TESTS

All of the steroids described in this invention are pharmacologically active compounds. The glucocorticoid activity of these products was studied in comparison with that of budesonide: pregna-1,4-diene- 3,20-dione, 16,17-butylidenebis(oxy)-11-21-dihydroxy-( 11β,16α). The pharmacologic action on the acetonides triamcinolone acetonide and flunisolide was also studied.

Anti-inflammatory effects of the compounds were screened in the cotton pellet granuloma bioassay for identification of lead compounds. (Meier et al., *Eperimentia* 6, 469, 1950). Male Wistar rats were used, ranging in weight between 90 and 120 g, at the rate of 10 animals per group, previously identified and quartered in individual cages. The animals had free access to feed and drink throughout the trial.

Cotton pellets weighing exactly 20 mg were prepared, sterilized for 2 hr. at 160° C. soaked with 50 λl solution of the product or with the solvent before implantation, and subsequently the solvent is evaporated before application. The implantation was performed subcutaneously in the axillary zone of the animals previously anesthetized with ether (right axilla pellet with product, left axilla pellet with solvent). Animals in which pellets without product were implanted were used as controls.

The drug was applied in alcohol solution at 4 dosage levels. Once the pellets were implanted, the animals were kept under normal rearing conditions, isolated for 7 days and then weighed, after which they were sacrificed by exsanguination.

Extraction and weighing of the thymus and adrenals were performed in all animals and a fluorometric determination of the cortisol plasma levels was made. We consider the variation in these parameters indicative of the systemic glucocorticoid activity of the products.

The topical activity was determined by the inhibitory effect on the weight of the cotton-pellet-induced granuloma; the granulomas were extracted and weighed (pellet and connective tissue surrounding them, dried for 24 hr in a 60° oven, and weighed).

The results are in the Tables IIIa and IIIb.

Anti-inflammatory $ED_{50}$ (topical effect), thymus inhibition $ED_{50}$ (systemic effect), therapeutic index (systemic $ED_{50}$/topical $ED_{50}$), and the therapeutic index relative to budesonide (=1).

All of the $ED_{50}$ values were calculated from the linear regression lines with the confidence limits.

The products that are the object of the present invention have shown in the pharmacologic studies performed a low systemic effect in relation to the topical pharmacologic activity found. The difference becomes even more evident when the reference products, budesonide, flunisolide, and triamcinolone acetonide are compared; effective local pharmacologic activity and low systemic glucocorticoid response are demonstrated.

TABLE I

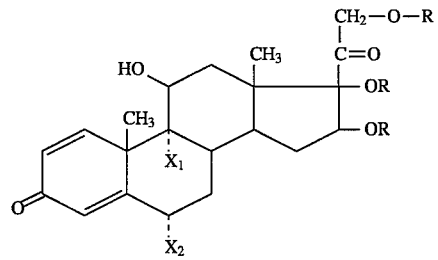

| COMPOUND | $X_1$ | $X_2$ | R | IR (ester) $(cm^{-1})$ | NMR $CH_3-C$ (ester) $\delta(^3ppm)$ |
|---|---|---|---|---|---|
| 1 | H | H | $-COCH(CH_3)CH_3$ | 1720,1270 | 1.17(d)–1.00(d)–0.98(d) |
| 2 | F | F | $-COCH(CH_3)CH_3$ | 1720,1250 | 1.16(d)–1.07(d)–0.95(d) |
| 3 | H | F | $-COCH(CH_3)CH_3$ | 1730,1230 | 1.18(d)–1.09(d)–0.93(d) |
| 4 | H | H | $-COCH_3$ | 1740,1228 | 2.50–1.96–1.94 |
| 5 | F | F | $-COCH_3$ | 1740,1230 | 2.02–2.01–1.92 |
| 6 | H | F | $-COCH_3$ | 1740,1230 | 2.01–1.98–1.90 |

TABLE II

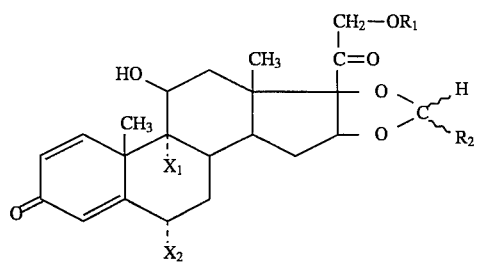

| COMPOUND | $X_1$ | $X_2$ | $R_1$ | $R_2$ | EPIMERS | R-S PROPORTION R | R-S PROPORTION S | NMR* 18-CH$_3$** δ(ppm) |
|---|---|---|---|---|---|---|---|---|
| 7 | H | H | —COOCH(CH$_3$)CH$_3$ | cyclohexyl | 22-R + S | 40–60% | 60–40% | |
| 8 | H | H | —COCH(CH$_3$)CH$_3$ | cyclohexyl | 22-S | 98–99% | 1–0% | 0.96 |
| 9 | H | H | —COCH(CH$_3$)CH$_3$ | cyclohexyl | 22-R | 99.9% | 0% | 0.94 |
| 10 | H | H | —COCH$_3$ | —CH$_2$—CH$_2$—CH$_2$—CH$_3$ | 22-R + S | 40–60% | 60–40% | |
| 11 | H | H | —COCH$_3$ | —CH$_2$—CH$_2$—CH$_2$—CH$_3$ | 22-S | 99% | 1% | 0.97 |
| 12 | H | H | —COCH$_3$ | —CH$_2$—CH$_2$—CH$_2$—CH$_3$ | 22-R | 99.9% | 0% | 0.93 |
| 13 | F | F | —COCH(CH$_3$)CH$_3$ | cyclohexyl | 22-R + S | 40–60% | 60–40% | |
| 14 | F | F | —COCH(CH$_3$)CH$_3$ | cyclohexyl | 22-S | 99–99.5% | 0% | 0.95 |
| 15 | F | F | —COCH(CH$_3$)CH$_3$ | cyclohexyl | 22-R | 99.9% | 0% | 0.93 |

*5% solution in Cl$_3$CD.
**Ref. TMS.

TABLE III

| | | LOCAL PHARMACOLOGIC ACTIVITY AND SYSTEMIC GLUCOCORTICOID EFFECTS EXPRESSED AS ED$_{50}$ μg/pellet | | | |
|---|---|---|---|---|---|
| COMPOUND | EPIMER | TOPICAL ANTI-INFLAMMATORY ACTIVITY (Cotton Pellet) | SYSTEMIC GLUCOCORTICOID ACTIVITY (Thymus inhibition) | THERAPEUTIC INDEX SYSTEMIC ED$_{50}$/ TOPICAL ED$_{50}$ | THERAPEUTIC INDEX WITH RESPECT TO BUDESONIDE |
| 7 | 22 R,S | 21.7 (17–27.7) | 614.7 (279.6–1351) | 28.3 | 26 |
| 8 | 22 S | 20.5 (16.9–25.6) | 608 (359.3–1228.3) | 29.6 | 27.2 |
| 9 | 22 R | 25.4 (18.2–31.1) | 667.1 (321.4–1489.2) | 26.2 | 24.5 |
| 10 | 22 R,S | 59.9 (59.3–60.3) | 583.2 (236.2–1440) | 9.7 | 8.9 |
| 11 | 22 S | 43 (38.4–58) | 555.3 (296.3–1387.3) | 12.9 | 11.8 |

TABLE III-continued

| | | LOCAL PHARMACOLOGIC ACTIVITY AND SYSTEMIC GLUCOCORTICOID EFFECTS EXPRESSED AS ED$_{50}$ μg/pellet | | | |
|---|---|---|---|---|---|
| COMPOUND | EPIMER | TOPICAL ANTI-INFLAMMATORY ACTIVITY (Cotton Pellet) | SYSTEMIC GLUCOCORTICOID ACTIVITY (Thymus inhibition) | THERAPEUTIC INDEX SYSTEMIC ED$_{50}$/ TOPICAL ED$_{50}$ | THERAPEUTIC INDEX WITH RESPECT TO BUDESONIDE |
| 12 | 22 R | 74.7 (85.3–65.1) | 592.2 (265.1–1342.9) | 7.9 | 7.2 |
| 13 | 22 R,S | 4.5 (3.7–5.5) | 54 (35–83.3) | 12 | 11 |
| 14 | 22 S | 3.6 (3–4.5) | 49 (30.7–76.2) | 13.6 | 15 |
| 15 | 22 R | 5.2 (3.6–6) | 56.3 (29.8–88.3) | 10.8 | 9.9 |
| BUDESONIDE | 22 R,S | 163.6 (125.1–213.9) | 178.6 (81.3–392.6) | 1.09 | 1 |
| TRIAMCINOLONE ACETONIDE | 22 R,S | 220.7 (198.1–245.7) | 156.4 (144.7–169) | 0.7 | 0.6 |
| FLUNISOLIDE | 22 R,S | 351.6 (268.8–459.9) | 156 (188.3–224.8) | 0.44 | 0.4 |

We claim:

1. A compound of the formula

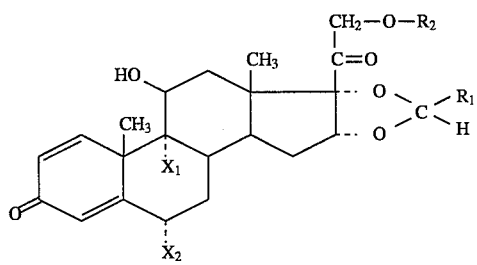

in the form of an R epimer, an S epimer, or a stereoisomeric mixture of the R and S epimers in terms of the orientation of the substituents on the carbon atom at position 22, wherein:

$R_1$ is cyclohexyl, $R_2$ is a member selected from the group consisting of

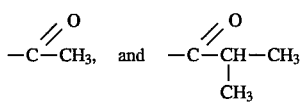

and wherein $X_1$ and $X_2$ may be the same or different and each is a member selected from the group consisting of hydrogen and fluorine.

2. A compound according to claim 1 in the form of the (22S)- epimer.

3. A compound according to claim 1 in the form of the (22R)- epimer.

4. An anti-inflammatory drug containing a compound according to claim 1.

5. A method of treating inflammatory conditions which comprises administering to a patient an anti-inflammatory effective amount of a compound according to claim 1.

6. A pharmaceutical composition having anti-inflammatory properties comprising as the active ingredient an effective amount of a compound according to claim 1 together with a pharmaceutically acceptable carrier.

7. A method for the treatment and control of inflammatory conditions characterized by the topical administration to a patient of an effective dose of a compound according to claim 1.

8. The compound of claim 1 which is [11β,16α(R,S)]-16,17-[ cyclohexylmethylene)bis (oxy)]-11-hydroxy-21-(2-methyl- 1-oxopropoxy)pregna-1,4-diene-3,20-dione.

9. The R-epimer of the compound of claim 8.

10. The S-epimer of the compound of claim 8.

11. A compound of claim 1 wherein each of is $X_1$ and $X_2$ is hydrogen.

12. A compound of claim 1 wherein each of $X_1$ and $X_2$ is fluorine.

* * * * *

UNITED STATES PATENT AND TRADEMARK OFFICE
CERTIFICATE OF CORRECTION

PATENT NO. : 5,482,934
DATED : January 9, 1996
INVENTOR(S) : CALATAYUD ET AL

It is certified that error appears in the above-identified patent and that said Letters Patent is hereby corrected as shown below:

Title page, Item: [73] "Especialidades Latinas Medicamentos Universales, S.A. (Elmu, S.A.)" should read --Elmuquimica Farmaceutica--.

Signed and Sealed this

Third Day of February, 1998

BRUCE LEHMAN

Attest:

Attesting Officer

Commissioner of Patents and Trademarks